US009901612B2

(12) United States Patent
Lingwood

(10) Patent No.: US 9,901,612 B2

(45) Date of Patent: Feb. 27, 2018

(54) USE OF A HOLOTOXIN TO REDUCE ENDOPLASMIC RETICULUM-ASSOCIATED DEGRADATION OF MISFOLDED PROTEINS

(71) Applicant: THE HOSPITAL FOR SICK CHILDREN, Toronto (CA)

(72) Inventor: Clifford Lingwood, Toronto (CA)

(73) Assignee: THE HOSPITAL FOR SICK CHILDREN, Toronto (CA)

( * ) Notice: Subject to any disclaimer, the term of this patent is extended or adjusted under 35 U.S.C. 154(b) by 0 days.

(21) Appl. No.: 14/309,558

(22) Filed: Jun. 19, 2014

(65) Prior Publication Data

US 2014/0371130 A1 Dec. 18, 2014

Related U.S. Application Data

(63) Continuation of application No. 13/393,082, filed as application No. PCT/CA2010/001360 on Aug. 27, 2010, now abandoned.

(60) Provisional application No. 61/237,910, filed on Aug. 28, 2009.

(51) Int. Cl.
*A61K 38/00* (2006.01)
*A61K 38/16* (2006.01)

(52) U.S. Cl.
CPC .................................. *A61K 38/164* (2013.01)

(58) Field of Classification Search
None
See application file for complete search history.

(56) References Cited

FOREIGN PATENT DOCUMENTS

| | | | |
|---|---|---|---|
| EP | 1 496 116 | A1 | 1/2005 |
| WO | 95/05810 | A1 | 3/1995 |
| WO | 2005/115429 | A1 | 12/2005 |
| WO | 2009/100037 | A1 | 8/2009 |

OTHER PUBLICATIONS

Nunnally et al eds. Vaccine Analysis: Strategies, Principles, and Control; Springer 2015, p. 237.*

Valle et al (Current Molecular Medicine, 12:860-871, 2012).*

Roomans, G. Am. J. Respir. Med. 2(5):413-431, 2003.*

Proesmans et al (Eur. J. Pediatr, 167:839-849, 2008).*

Dawson et al (PLOS ONE 8:e74347-e74347, 2013.*

Barriere et al (Prog. Repir. Res., Basel, Karger 2006, 34:21-28, 2006).*

Bergan et al. (Aug. 16, 2012) "Shiga toxins," Toxicon. 60:1085-1107.

Chen et al. (2005) "ER-associated protein degradation is a common mechanism underpinning numerous monogenic diseases including Robinow syndrome," Human Molecular Genetics. 14(17):2559-2569.

Chelra (2005) "Shiga toxin 1-induced cytokine production is mediated by MAP kinase pathways and translation initiation factor eIF4E in the macrophage-like THP-1 cell line," Journal of Leukocyte Biology Society for Leukocyte Biology. 79(2):397-407.

Deeks et al. (2002) "The low lysine content of ricin A chain reduces the risk of proteolytic degradation after translocation from the endoplasmic reticulum to the cytosol," Biochemistry. 41(10):3405-3413.

Hazes et al. (1997) "Accumulating Evidence Suggest That Several AB-Toxins Subvert the Endoplasmic Reticulum-Associated Protein Degradation Pathway to Enter Target Cells," Biochemistry. 36(37):11051-11054.

Hebert et al. (2007) "In and Out of the ER: Protein Folding, Quality Control, Degradation, and Related Human Diseases," Physiological Reviews. 87(4):1377-1408.

Lingwood (1999) "Glycolipid receptors for verotoxin and Helicobacter pylori: role in pathology," Biochimica et Biophysica Acta. 1455:375-386.

Lord et al. (2005) "Entry of protein toxins into mammalian cells by crossing the endoplasmic reticulum membrane: co-opting basic mechanisms of endoplasmic reticulum-associated degradation," Current Topics in Microbiology and Immunology. 300:149-168.

Park et al. (2009) "A Soluble Sulfogalactosyl Ceramide Mimic Promotes AF508 CFTR Escape from Endoplasmic Reticulum Associated Degradation," Chemistry & Biology. 16(4):461-470.

Rutjes et al. (2002) "Differential tissue targeting and pathogenesis of verotoxins 1 and 2 in the mouse animal model," Kidney International. 62:832-845.

Schmitz et al. (2000) "Cholera Toxin Is Exported from Microsomes by the Sec61p Complex," The Journal of Cell Biology. 148:1203-1212.

Scott et al. (2008) "Role of Sec61p in the ER-Associated Degradation of Short-Lived Transmembrane Proteins," The Journal of Cell Biology. 181(7):1095-1105.

Tam et al. (2007) "Membrane-cytosolic translocation of verotoxin AI subunit in target cells," Microbiology. 153:2700-2710.

Vago et al. (2005"Saporin and ricin A chain follow different intracellular routes to enter the cytosol of intoxicated cells," FEBS J. 272(19):4983-4995.

Wen et al. (2006) "Genetic toxoids of Shiga toxin types 1 and 2 protect mice against homologous but not heterologous toxin challenge," Vaccine. 24(8):1142-1148.

Wiertz et al. (1996) "Sec61-mediated transfer of a membrane protein from the endoplasmic reticulum to the proteasome for destruction," Nature. 384:432-438.

International Search Report with Written Opinion corresponding to International Patent Application No. PCT/CA2010/001360, mailed Dec. 21, 2010.

* cited by examiner

*Primary Examiner* — Patricia Duffy

(74) *Attorney, Agent, or Firm* — Lathrop Gage LLP; Brian C. Trinque

(57) ABSTRACT

The present invention provides a method of blocking endoplasmic reticulum associated degradation of functional but misfolded proteins.

6 Claims, 4 Drawing Sheets

1. no transfection
2. no VT treatment
3. 100ng VT1, 2hrs
4. inactive VT 1.0μg, 2hrs
5. inactive VT 3.0μg, 2hrs

USE OF A HOLOTOXIN TO REDUCE ENDOPLASMIC RETICULUM-ASSOCIATED DEGRADATION OF MISFOLDED PROTEINS

CROSS-REFERENCE TO RELATED APPLICATIONS

The present application is a continuation application of U.S. Ser. No. 13/393,082 filed Apr. 25, 2012, which was a national entry application based on PCT/CA2010/001360 filed Aug. 27, 2010, which claimed priority to U.S. Provisional application No. 61/237,910 filed Aug. 28, 2009.

FIELD OF THE INVENTION

The invention relates to a method of blocking ER associated degradation of misfolded proteins. The invention further relates to the use of a holotoxin to block ERAD mediated degradation of misfolded proteins.

BACKGROUND OF THE INVENTION

The endoplasmic reticulum plays a key role in the quality control of protein translation and posttranslational modification. Many systems within the ER are present for the detection of misfolded proteins. The selection for complexation and elimination by proteolytic degradation following retrotranslocation from the ER to the cytosol is the central tenet of this process (ERAD—Endoplasmic Reticulum associated degradation). This, in turn, regulates the unfolded protein response and other ER stress related signaling pathways.

In many, perhaps all, genetic diseases, mutations are present which do not affect the primary function of the given protein but cause some small changes in the folding of the protein within the ER, such that it is recognized as a misfolded protein to initiate this quality control mechanism, such that the protein is degraded and is not permitted to mature through anterograde transport through the Golgi/TGN/secretory vesicles to the cell surface or secretion.

Many ingenious procedures have been described which attempt to rescue such functional but nevertheless misfolded and degraded mutant proteins, to allow ERAD escape, maturation and trafficking to the correct location for functional reversal of the pathogenic phenotype. These include the use of chemical chaperones, chaperone inhibitors, enzyme substrates or inhibitors. Diseases in which such approaches are heavily studied include arthritis, cystic fibrosis, lysosomal storage diseases, aspects of dislipidemia, hypertension, cholesterol biosynthesis and $\alpha$1-antitripsin disease.

SUMMARY OF THE INVENTION

Given the significance of ERAD in disease, it would be desirable to develop methods that block ERAD-mediated degradation of misfolded proteins.

It has now been found that a holotoxin is effective to block ERAD-mediated misfolded protein degradation.

Thus, in one aspect, the use of a holotoxin in which the A subunit may optionally be inactivated to block ERAD mediated misfolded protein degradation is provided.

The present invention further provides the use of a holotoxin in which the A subunit has optionally been inactivated to partially block the ER translocon and thereby block ERAD mediated misfolded protein degradation.

The present invention further provides the use of a holotoxin in which the A subunit has optionally been inactivated as a competitive inhibitor of ER translocon occupancy.

The present invention further provides the use of a holotoxin in which the A subunit has optionally been inactivated to rescue functional misfolded proteins from ER associated degradation.

BRIEF DESCRIPTION OF THE DRAWINGS

The present invention will now be described in further detail with reference to the following figures.

DETAILED DESCRIPTION OF THE PREFERRED EMBODIMENTS

The present invention provides the use of a holotoxin in which the A subunit has optionally been inactivated to retrograde transport from the cell surface to the ER and partially block the ER-located Sec61 translocon, to allow partially misfolded but functionally competent mutant proteins to escape ER associated degradation (ERAD) and rescue the defective cellular phenotype.

Any holotoxin which undergoes retrograde transport to the ER where the proteolytically activated A subunit separates from the B subunits and is translocated into the cytosol via the Sec61 translocon may be employed for use to rescue partially misfolded but functionally competent mutant proteins to escape ER associated degradation (ERAD). Examples of suitable holotoxins for use in accordance with the present invention include ricin, shiga or shiga-like toxins (such as verotoxin—VT1), cholera toxin, abrin' modeccin *Pseudomonas* exotoxin A and plasmid-encoded toxin (Pet) of enteroaggregative *Escherichia coli*. Cell surface bound cholera toxin, verotoxin and ricin all undergo retrograde transport to the ER where the proteolytically activated A subunit separates from the B subunits and is translocated into the cytosol via the Sec61 translocon. This is the same translocon utilized in the ER associated degradation pathway to remove unfolded proteins for ubiquitination and cytosolic digestion by the proteosome.

Figure 1:
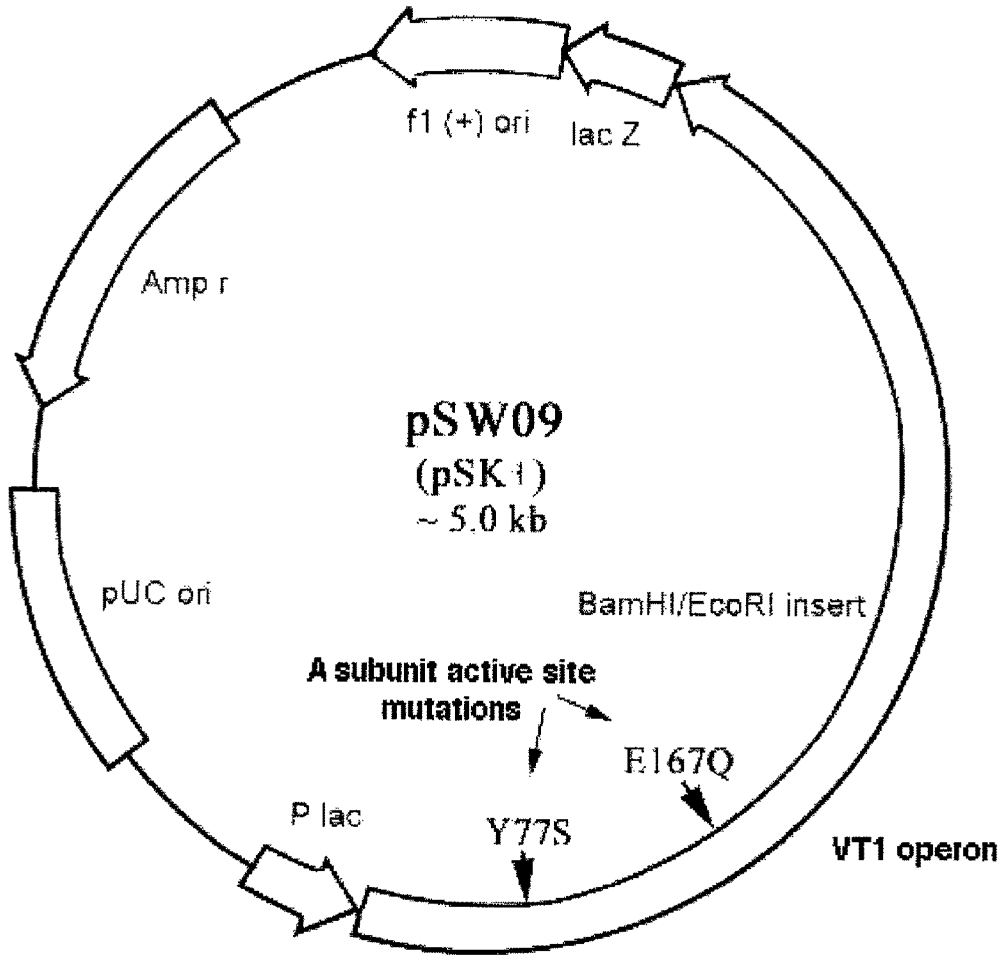
FIG. 1 illustrates a plasmid showing inactivated A subunit containing VT1 according to one embodiment of the present invention.

The A subunit of the selected holotoxin may be inactivated for use according to the present invention. Methods of inactivating the A subunit of a holotoxin are well-established in the art and include, for example, mutating residues within the A subunit that are required for subunit A activity. In one embodiment of the present invention, a non-toxic verotoxin 1, mutated in crucial residues in the A subunit active site, e.g. mutations such as Y77S and E167Q, is suitable for use. Variations to the above referenced mutations, and in particular to the amino acids used in the above referenced mutations, and those shown in FIG. 1, may also be made provided that the mutations inactivate the A subunit.

The A subunit is translocated into the cytosol but cannot inhibit protein synthesis. Thus, the A subunit, optionally inactivated, functions as a competitive inhibitor of translocon occupancy in order to effect rescue of a partially misfolded but functionally competent mutant protein from ERAD. For example, the A subunit of verotoxin 1, optionally inactivated, is effective to rescue mutant ΔF508CFTR.

The A subunit may be further modified, by means known in the art, to provide a more efficient inhibitor of the translocon and improved blocking of ERAD. Suitable modifications include addition the addition of an entity, such as a peptide sequence, to the A subunit which further enhances the function of the A subunit to inhibit the translocon. For example, a hexahistidine sequence, shown to block the diptheria toxin channel or a 18-25 apolar peptide sequence—a stop transfer sequence—from translocated secretory/membrane proteins (e.g. from glycophorin or the LDL receptor) could be added to attempt to block translocon passage. Another approach includes coupling of a Sec61 inhibitor, such as CAM741, to the A subunit, or coupling of an inhibitor that blocks endoplasmic reticulum (ER)-associated protein degradation such as the chemical inhibitor, Eeyarestatin I (EerI).

As stated above, in one embodiment, the present invention provides the use of verotoxin, also referred to as Shiga-toxin and Shiga-like toxin, and in particular a non-toxic mutated A subunit of verotoxin, as a mechanism to target the ER to functionally rescue genetically misfolded but functional proteins by blocking the translocon. The term "intracellular surgery" might be used to describe the process discussed herein.

In an alternative embodiment, a cholera toxin including a non-toxic mutated A subunit is used, as described herein. In an alternative embodiment, a ricin toxin including a non-toxic mutated A subunit is used, as described herein. It will be understood by the above, that while the embodiment of the present invention that utilizes a mutated A subunit of verotoxin may only comprise the mutated A subunit, the cholera and ricin toxins will include the B subunits and the mutated A subunits.

In another embodiment, Fab antibody fragments or their phage analogues may be targeted to the ER for selective delivery of binding proteins within the subcellular compartment.

The present invention further includes the use of modifications of the A subunit to increase retention within the translocon to increase the efficacy of the approach described herein. The present invention also includes the use of such A subunit chimeras transferred into an inactivated ricin toxin to provide a more broadly based therapy to reduce ERAD of partially misfolded proteins in any tissue. In addition, the present invention provides an A subunit, as described herein, that can be further modified to transport various molecules which might be beneficial to ameliorate defects of protein trafficking, function, sorting, glycosylation and other post-translational modifications, including chaperones that assist mutant protein folding within the lumen of the endoplasmic reticulum, e.g. ambroxol which stabilizes mutant glucocerebrosidase in Gaucher's disease.

A method of treating a disease resulting from or otherwise arising from ERAD, e.g. an ERAD-related disease, is also provided. The method comprises administration to a subject, such as a mammal or non-mammal, of a holotoxin in which the A subunit is optionally inactivated. The term "mammal" is used herein to refer to human and non-human mammals, e.g. cats, dogs and horses.

ERAD-related diseases are diseases in which ERAD itself is essentially the instigator of disease, whereby functional, but partially misfolded mutant proteins are eliminated leading to disease symptoms. In some diseases ERAD degradation removes a slightly misfolded, but otherwise functional protein, to result in a pathological condition. All such diseases are candidates for therapy based on the translocon blockage approach described herein. Thus, ERAD-related disease, includes but is not limited to, arthritis, cystic fibrosis, glycosphingolipid lysosomal storage diseases, aspects of dislipidemia, hypertension, cholesterol biosynthesis, α1-antitripsin disease, Gaucher's disease and disease from HIV infection. Other ERAD-related diseases that are candidates for therapy based on the approach disclosed herein are shown in Table 1 below, previously shown in Human Molecular Genetics 2005 14 (17):2559-2569. The genes listed in Table 1 are those identified as strong ER-retention candidates. They include diseases where the location of the mutation or experimental data suggest a defect in folding or trafficking. It will be understood that the diseases listed herein include some of the known diseases that are currently associated with ERAD degradation. It will be understood that any and all diseases that are found to be associated with ERAD degradation are also contemplated within the scope of the present invention.

TABLE 1

| Gene | Disease | System affected | Potential effect of pathogenic mutation(s) |
|---|---|---|---|
| ROR2 | Robinow syndrome | Skeletal, heart | Disruption to protein folding |
| POMTI | Walker-Warburg syndrome | Musculoskeletal | Disruption to TMD |
| GUCY2D | Leber congenital amaurosis, type 1 | Ocular | Possible retention in the ER reported[a] |
| COLQ | Endplate acetyl-cholinesterase deficiency | Muscular | Disruption to protein folding |
| MPZ | Charcot-Marie-Tooth neuropathy-IB | Neurological | Possible retention in the ER reported[b] |
| SLC2A1 | Glucose transport defect | Blood-brain barrier | Disruption to TMD |
| CSF2RB | Pulmonary alveolar proteinosis | Lung | Disruption to tertiary structure |
| ACVRL1 | Hereditary hemorrhagic telangiectasia | Vascular/pulmonary | Possible retention in the ER reported[c] |
| BMPR2 | Family primary pulmonary hypertension | Vascular/pulmonary | Disruption to protein folding |
| GJB3 | Erythrokeratodermia variabilis | Skin | Possible retention in the ER reported[d] |
| GJB4 | Erythrokeratodermis variabilis | Skin | Disruption to TMD |
| ABCA1 | Tangier disease and HDL deficiency | Cardiovascular | Disruption to protein folding[e] |
| DHCR7 | Smith-Lemli-Opitz syndrome | Cardiovascular | Disruption to protein folding |
| DHCR24 | Desmosterolosis | Cardiovascular | Disruption to protein folding |
| ELN | Supravalvular aortic stenosis | Cardiovascular | Disruption to protein folding |

The holotoxin may be administered alone or in combination with at least one pharmaceutically acceptable adjuvant. The expression "pharmaceutically acceptable" means acceptable for use in the pharmaceutical and veterinary arts, i.e. not being unacceptably toxic or otherwise unsuitable. Examples of pharmaceutically acceptable adjuvants include diluents, excipients and the like. Reference may be made to "Remington's: The Science and Practice of Pharmacy", 21st Ed., Lippincott Williams & Wilkins, 2005, for guidance on drug formulations generally. The selection of adjuvant depends on the intended mode of administration of the composition. In one embodiment of the invention, the compounds are formulated for administration by infusion, or by injection either subcutaneously or intravenously, and are accordingly utilized as aqueous solutions in sterile and pyrogen-free form and optionally buffered or made isotonic. Thus, the compounds may be administered in distilled water or, more desirably, in saline, phosphate-buffered saline or 5% dextrose solution. Compositions for oral administration via tablet, capsule or suspension are prepared using adjuvants including sugars, such as lactose, glucose and sucrose; starches such as corn starch and potato starch; cellulose and derivatives thereof, including sodium carboxymethylcellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil and corn oil; polyols such as propylene glycol, glycerine, sorbital, mannitol and polyethylene glycol; agar; alginic acids; water; isotonic saline and phosphate buffer solutions. Wetting agents, lubricants such as sodium lauryl sulfate, stabilizers, tableting agents, antioxidants, preservatives, colouring agents and flavouring agents may also be present. Creams, lotions and ointments may be prepared for topical application using an appropriate base such as a triglyceride base. Such creams, lotions and ointments may also contain a surface active agent. Aerosol formulations, for example, for nasal delivery, may also be prepared in which suitable propellant adjuvants are used. Other adjuvants may also be added to the composition regardless of how it is to be administered, for example, anti-microbial agents may be added to the composition to prevent microbial growth over prolonged storage periods.

In addition, the present invention provides for the control of the dosage of the mutant or non-mutant A subunit containing holotoxin that is used. The holotoxin dosage may be adjusted so that competitive inhibition is partial. In some applications up to about 10% ERAD escape could be sufficient to correct the defective phenotype and dosages appropriate to achieve this correction may be readily determined by one of skill in the art. As will be understood by one of skill in the art, the dosage may vary with the holotoxin being used, the disease or condition being treated and the subject being treated. In one embodiment, holotoxin dosages in the range of about 1-100 ng/kg, e.g. 10 ng/kg, may be utilized.

One application of the present invention provides a viable new approach to the rescue of the ΔF508 CFTR mutation to increase chloride transport in CF cells. The present invention provides a new therapeutic approach to the most common mutation in cystic fibrosis.

The A subunit containing holotoxins described herein may also be used as antidotes to the parental toxins since ER translocation of the wild type A subunit will be prevented due to the partial blocking, by the catalytically inactivated A subunit containing holotoxin, of the translocon. In one embodiment of the present invention the inactivated A subunit containing holotoxin includes a stop transfer sequence. Examples of the type of stop transfer sequence include, but are not limited to, VFIVSVGSFITSVLFIVI (SEQ ID NO: 8) or stop transfer sequences having 9-18 leucine residues. Variations to the length of the above sequence may also be made and the extensions may be added in two steps.

The present invention also provides a VT1 holotoxin A subunit with the addition of a polyleucine stop transfer sequence. The stop transfer sequence may be added to the N-terminus of the inactivated VT1 A subunit. Stop transfer sequences generally comprise about 9-18 hydrophobic amino acid residues. This sequence may be added to the N-terminus of the VT1 A subunit to increase the efficiency of translocon blockade. Furthermore, addition of two basic amino acids to the C terminus of the stop transfer sequence increases stop translocation efficiency. Therefore, two lysines may also be added at the C terminus of the polyleucine stop transfer addition. In contrast, addition of C terminal negative amino acid residues have been shown to reduce stop translocation efficiency. Therefore, the addition of a stop transfer sequence to the VT1 A subunit may reduce the bacterial synthesis of the modified holotoxin. Placement of negative charges at the C terminus and positive charges at the N terminus of the polyleucine insert may favour stop transfer function during retrograde, rather than antegrade transit through the Sec61 translocon, i.e. the stop transfer sequence should have minimum effect during toxin bacterial synthesis but maximum effect when targeted to the ER and retrotranslocated through the translocon to the cytosol, although the orientation of the VT1 A subunit when it enters the translocon (i.e. N- or C-terminus first) is not known. The present invention includes constructs in which the basic dilysine motif is included at the C terminus and an acidic aspartic acid dimer incorporated at the N terminus of the polyleucine insert and vice versa. The holotoxin constructs may be expressed in vector, such as puc19, and the holotoxin made may be purified by B subunit mediated $Gb_3$ affinity chromatography, as described in Noakes K L et al., 1999 and Boulanger J, Huesca M, Arab S, Lingwood C A. Universal method for the facile production of glycoplid/lipid matrices for the affinity purification of binding ligands. Anal Biochem. 1994; 217:1-6.

Stop transfer efficacy approximately corresponds to the hydrophobicity of the amino acid sequence but variations and exceptions do exist, as described in Saaf A., Wallin E, von Heijne G. Eur J Biochem 1998; 251:821-829. The stop transfer sequence CFIVSVGSFITSVLFIVI (SEQ ID NO: 9), may be fused to the VT1 A subunit, again in both orientations. PCR primer extension technology may be used to add the sequence to the 5' end of the VT1 A subunit gene. The whole sequence may be made in two steps, adding 9 amino acids in each. The holotoxin may be purified by affinity chromatography as described above.

The present invention will now be described in the following examples which are not to be construed as limiting.

Example 1—Use of VT1 to Rescue ΔF508CFTR from Degradation

Treatment of ΔF508CFTR expressing HeLa cells with wild-type VT1 or an inactive VT1, as described above, (catalytic residues in the A subunit required for the depurination mutated) showed clear rescue of ΔF508CFTR from degradation early, within 2-4 hours of toxin treatment.

Figure 2:
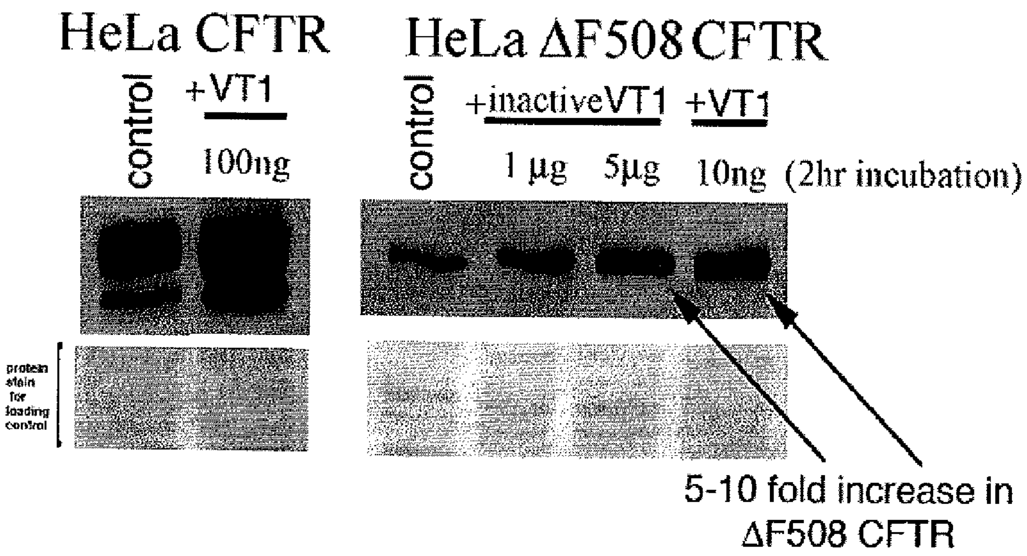
FIG. 2 is a western blot that shows VT and inactivated VT1 protects ΔF508CFTR from ERAD.

As shown in FIG. 2, HeLa cells transfected to express wild-type CFTR or ΔF508CFTR were treated with verotoxin 1 or VT1 containing an inactivated A subunit. The inactivated toxin preparation was less pure than the wild-type VT1 and was therefore used at a higher concentration. The level of expression of CFTR was determined by Western blot of the cell extract. In wild-type CFTR expressing cells, the immature (core glycosylated) and mature upper lactosamine glycosylated species of CFTR are detected. For ΔF508CFTR only the lower, core glycosylated species is detected. Wild-type CFTR is subject to ERAD and treatment with VT1 results in a slight increase in wild-type CFTR due to ERAD blockage. For ΔF508CFTR both the inactivated and the wild-type VT1 induced up to 10-fold increase in the level of expression as compared to untreated control cells indicating significant escape from ERAD.

Example 2—Use of VT1 to Rescue an MDRI Mutant

Figure 3:
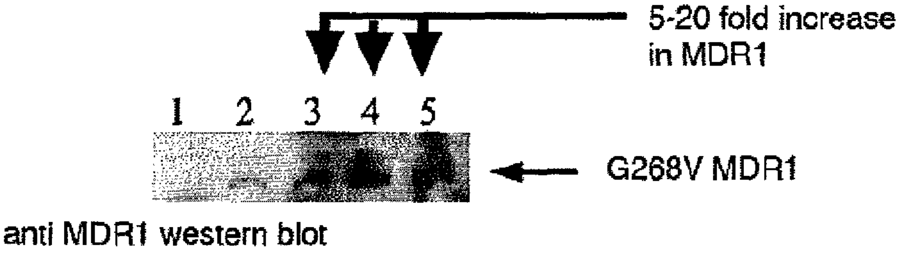
FIG. 3 is a western blot that shows VT and inactivated VT protect misfolded MDR1 from ERAD.

To further confirm the inhibition of ERAD, the effect of VT1 and inactive mutant VT1 on HeLa cells transfected to express a misfolded mutant (G268V) of MDR1, the drug efflux pump (described in Loo T W, Clarke D M, FASEB J 1999; 13:1724-1732). Again, both VT1 and mutant VT1 induced the accumulation of MDR1 which was otherwise degraded by ERAD, as shown in FIG. 3. A 5-20 fold increase in the level of the G268V MDR1 mutant expressed in HeLa cells was observed following 2 hr treatment with either wild-type or inactivated VT1 holotoxin.

Example 3—Use of Cholera Toxin to Rescue ΔF508CFTR

Figure 4:
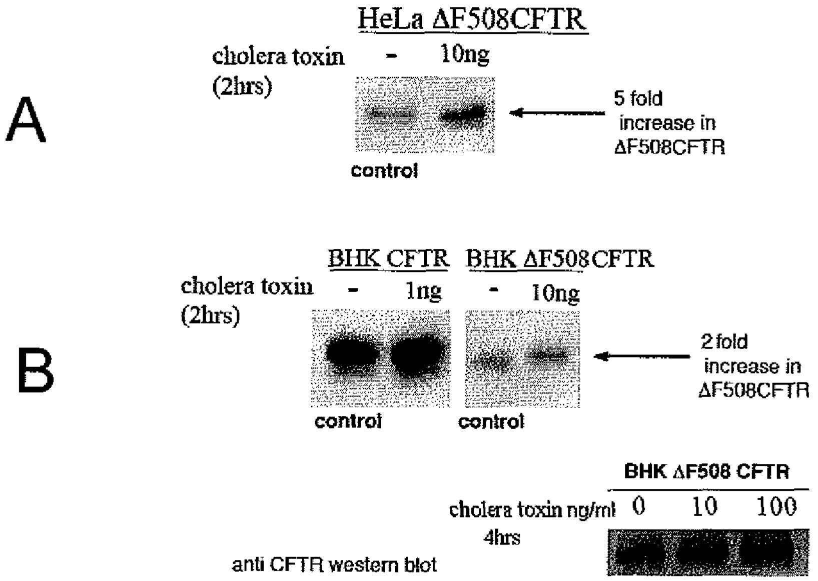
FIG. 4 is a western blot that shows cholera toxin protects ΔF508CFTR from ERAD in both HeLa and BHK cells.

The effect of cholera toxin on the expression of ΔF508CFTR in BHK cells, not sensitive to VT1 but, like most cells, sensitive to cholera toxin, was determined. It was shown that the toxin induced ΔF508CFTR ERAD escape in these cells, as shown in FIG. 4. HeLa cells transfected with ΔF508CFTR in BHK cells transfected with wild-type or ΔF508CFTR were treated with cholera toxin for 2 hours and the level of wild-type or ΔF508CFTR monitored by western blot. 10 ng/ml cholera toxin induced up to 5-fold increase in ΔF508CFTR. The increase was seen both in BHK and HeLa cells since cholera toxin binds to GM1 ganglioside, expressed in both these cell lines.

Example 4—Use of VT1 to Rescue GCC in Gaucher Disease Cells

VT1 reduces ERAD of the enzyme GCC (glucocerebrosidase) in Gaucher's disease cells, allowing more of the enzyme to mature and potentially, reduce the glucosyl ceramide accumulation responsible for the disease.

Example 5—Construction of Stop-Transfer Sequence Containing Inactivated Verotoxin Two different constructs were made to generate stop-transfer amino acid containing inactivated verotoxin A protein. One had 9 leucine stop-transfer amino acids and the other construct had 18 random amino acids sequence. The two sets of PCR primers (Table 2) were used to generate each stop-transfer amino acid containing inactivated verotoxin A protein. The first PCR amplification introduced 9 leucine or 18 random amino acids into inactivated verotoxin A protein sequence using pSW09 plasmid (Vaccine 2006, 24:1142). The second PCR used two outer primers and amplified entire inactivated verotoxin A protein containing stop transfer amino acid. Plasmid pSW09 has two mutations in VTA sequence: Y77S and E167Q. The DNA fragments were digested with BamHI and EcoRI and ligated into pSK+ (Stratagene). The resulting plasmids were stop-transfer sequence containing mutant verotoxin A.

Construction of Stop-Transfer Amino Acids Containing Inactivated VTA Protein

Two different constructs are made to generate stop-transfer amino add containing inactivated verotoxin A protein. One has 9 leucine stop-transfer amino acids (*JBC,* 1991, 266:9251) and the other construct has 18 random amino acids sequence (*EJB,* 1998, 251:821). The two sets of PCR primers (Table 1) are used to generate each stop-transfer amino acid containing inactivated verotoxin A protein. The first PCR amplification introduces 9 leucine or 18 random amino acid into inactivated verotoxin A protein sequence using pSW09 plasmid (*Vaccine* 2006, 24:1142). The second PCR uses two outer primers and amplifies entire inactivated verotoxin A protein containing stop transfer amino acid. Plasmid pSW09 has two mutations in VTA sequence: Y77S and E167Q. The DNA fragments are digested smith BamHI and EcoRI and ligated into pSK+ (Stratagene). The resulting plasmids are stop-transfer sequence containing mutant verotoxin A.

TABLE

Oligonucleotide set for introducing stop-transfer sequence

| Primers | Sequence | SEQ ID NO |
|---|---|---|
| 9 leucine-outer forward | 5'-GTGGATCCTCAAGGAGTATTG-3' | 1 |
| 9 leucine-inner reverse | 5'-CGAGAAGTCTAAGGTAAATTCCTT CAG GAG CAA CAG TAG AG GAG CAA CGCCACCACATTAACTGA-3' | 2 |
| 9 leucine-inner forward | 5'-TCAGTTAATGTGGTGGCG TTG(L) CTC(L) CTT(L) CTA(L) CTG(L) TTG(L) CTC(L) CTG(L) AAGGAATTTACCTTAGACTTCTCG-3' | 3 |
| 9 leucine-outer reverse | 5'-GTGAATTCAACAACTGACTG-3' | 4 |
| 18 random a.ac-outer forward | 5'-GTGGATCCTCAAGGAGTATTG-3' | 1 |
| 18 random a.ac-inner reverse | 5'-CGAGAAGTCTAAGGTAAATTCCTT GAT GAC GAT GAA AAG GAC ACT AGT CAT GAA ACT ACC CAC GCT GAC GAT GAA GAC CGCCACCACATTAACTGA-3' | 5 |
| 18 random a.ac-inner forward | 5'-TCAGTTAATOTGGTGGCG GTC(V) TTC(F) ATC(I) GTC(V) AGC(S) GTG(V) GGT(G) AGT(S) TTC(F) ATG(I) ACT(T) AGT(S) GTC(V) CTT (L) TTC(F) ATC(I) GTC(V) ATC(I) AAGGAATTTACCTTAGACTTCTCG-3' | 6 |
| 18 random a.ac-outer reverse | 5'-GTGGAATTCAACAACTGACTG-3' | 7 |

( ) denotes amino acid codon letter.

While this invention has been described with reference to illustrative embodiments and examples, the description is not intended to be construed in a limiting sense. Thus, various modification of the illustrative embodiments, as well as other embodiments of the invention, will be apparent to persons skilled in the art upon reference to this description. It is therefore contemplated that the appended claims will cover any such modifications or embodiments. Further, all of the claims are hereby incorporated by reference into the description of the preferred embodiments.

Any publications, patents and patent applications referred to herein are incorporated by reference in their entirety to the same extent as if each individual publication, patent or patent application was specifically and individually indicated to be incorporated by reference in its entirety.

The invention claimed is:

1. A method of reducing endoplasmic reticulum-associated degradation (ERAD) of misfolded functional proteins in a mammal having cystic fibrosis or Gaucher's disease comprising administering to the mammal an effective amount of a holotoxin comprising an inactivated A subunit wherein the holotoxin is shiga toxin or cholera toxin.

2. The method of claim 1, wherein the holotoxin is modified to include a stop transfer sequence at the N-terminus of the inactivated A subunit.

3. The method of claim 2, wherein the stop transfer sequence is selected from the group consisting of 9-18 hydrophobic amino acid residues, 9-18 leucine residues, the amino acid sequence of SEQ ID NO: 8 and the amino acid sequence of SEQ ID NO: 9.

4. The method of claim 3, wherein the stop transfer sequence comprises two basic amino acids at its C-terminus.

5. The method of claim 1, wherein the holotoxin is cholera toxin and the misfolded functional protein is a cystic fibrosis transmembrane regulator mutant.

6. The method of claim 1, wherein the holotoxin is shiga toxin and the misfolded functional protein is a glucocerebrosidase mutant.

* * * * *

SEQUENCE LISTING

```
<160> NUMBER OF SEQ ID NOS: 9

<210> SEQ ID NO 1
<211> LENGTH: 21
<212> TYPE: DNA
<213> ORGANISM: artificial
<220> FEATURE:
<223> OTHER INFORMATION: primer

<400> SEQUENCE: 1

gtggatcctc aaggagtatt g                                              21


<210> SEQ ID NO 2
<211> LENGTH: 65
<212> TYPE: DNA
<213> ORGANISM: artificial
<220> FEATURE:
<223> OTHER INFORMATION: primer

<400> SEQUENCE: 2

cgagaagtct aaggtaaatt ccttcaggag caacagtaga ggagcaacgc caccacatta     60

actga                                                                 65


<210> SEQ ID NO 3
<211> LENGTH: 66
<212> TYPE: DNA
<213> ORGANISM: artificial
<220> FEATURE:
<223> OTHER INFORMATION: primer

<400> SEQUENCE: 3

tcagttaatg tggtggcgtt gctccttcta ctgttgctcc tgaaggaatt taccttacac     60

ttctcg                                                                66


<210> SEQ ID NO 4
<211> LENGTH: 20
<212> TYPE: DNA
<213> ORGANISM: artificial
<220> FEATURE:
<223> OTHER INFORMATION: primer

<400> SEQUENCE: 4

gtgaattcaa caactgactg                                                 20


<210> SEQ ID NO 5
<211> LENGTH: 96
<212> TYPE: DNA
<213> ORGANISM: artificial
<220> FEATURE:
<223> OTHER INFORMATION: primer

<400> SEQUENCE: 5

cgagaagtct aaggtaaatt ccttgatgac gatgaaaagg acactagtca tgaaactacc     60

cacgctgacg atgaagaccg ccaccacatt aactga                               96
```

-continued

```
<210> SEQ ID NO 6
<211> LENGTH: 96
<212> TYPE: DNA
<213> ORGANISM: artificial
<220> FEATURE:
<223> OTHER INFORMATION: primer

<400> SEQUENCE: 6

tcagttaatg tggtggcggt cttcatcgtc agcgtgggta gtttcatgac tagtgtcctt     60

ttcatcgtca tcaaggaatt taccttagac ttctcg                               96


<210> SEQ ID NO 7
<211> LENGTH: 21
<212> TYPE: DNA
<213> ORGANISM: artificial
<220> FEATURE:
<223> OTHER INFORMATION: primer

<400> SEQUENCE: 7

gtggaattca acaactgact g                                               21


<210> SEQ ID NO 8
<211> LENGTH: 18
<212> TYPE: PRT
<213> ORGANISM: Artificial Sequence
<220> FEATURE:
<223> OTHER INFORMATION: stop transfer sequence

<400> SEQUENCE: 8

Val Phe Ile Val Ser Val Gly Ser Phe Ile Thr Ser Val Leu Phe Ile
1               5                   10                  15

Val Ile


<210> SEQ ID NO 9
<211> LENGTH: 18
<212> TYPE: PRT
<213> ORGANISM: Artificial Sequence
<220> FEATURE:
<223> OTHER INFORMATION: stop transfer sequence

<400> SEQUENCE: 9

Cys Phe Ile Val Ser Val Gly Ser Phe Ile Thr Ser Val Leu Phe Ile
1               5                   10                  15

Val Ile
```